United States Patent [19]

Sumner et al.

[11] Patent Number: 5,979,177
[45] Date of Patent: Nov. 9, 1999

[54] ETHYLENE PLANT REFRIGERATION SYSTEM

[75] Inventors: Charles Sumner, Livingston, N.J.; Vitus Tuan Wei, Houston, Tex.; John J. Crawford, Coraopolis, Pa.; Stephen J. Stanley, Matawan; Richard John McNab, Randolph, both of N.J.

[73] Assignee: ABB Lummus Global Inc., Bloomfield, N.J.

[21] Appl. No.: 09/003,432

[22] Filed: Jan. 6, 1998

[51] Int. Cl.$^6$ ........................................ F25J 1/00
[52] U.S. Cl. ................... 62/612; 62/619; 62/935
[58] Field of Search ............... 62/612, 619, 935

[56] References Cited

U.S. PATENT DOCUMENTS

| | | | |
|---|---|---|---|
| 5,253,479 | 10/1993 | Di Cinto et al. | 62/935 |
| 5,377,490 | 1/1995 | Howard et al. | 62/23 |
| 5,379,597 | 1/1995 | Howard et al. | 62/23 |
| 5,452,581 | 9/1995 | Dinh et al. | 62/935 |
| 5,497,626 | 3/1996 | Howard et al. | 62/23 |
| 5,502,972 | 4/1996 | Howard et al. | 62/23 |
| 5,611,216 | 3/1997 | Low et al. | 62/612 |

OTHER PUBLICATIONS

Kaiser, V., Salhi, O. and Pocini, C., "Analyze mixed refrigerant cycles", Hydrocarbon Processing, Jul. 1978, pp. 163–166.

Kaiser, V., Becdelievre, C. and Gilbourne, D.M., "Mixed refrigerant for ethylene", Hydrocarbon Processing, Oct. 1976, pp. 129–131.

Primary Examiner—Ronald Capossela
Attorney, Agent, or Firm—Alix, Yale & Ristas, LLP

[57] ABSTRACT

A refrigeration system for an ethylene plant uses a low pressure demethanizer and a binary refrigerant comprising a mixture of methane and ethylene or methane and ethane. The refrigeration composition may be constant throughout the system or separators may be used to divide the refrigerant into a methane-rich binary refrigerant and an ethylene- or ethane-rich binary refrigerant.

9 Claims, 3 Drawing Sheets

5,979,177

ETHYLENE PLANT REFRIGERATION SYSTEM

BACKGROUND OF THE INVENTION

The present invention pertains to a refrigeration system to provide the cooling requirements of an ethylene plant. More particularly, the invention is directed to the use of a binary refrigerant comprising a mixture of methane and ethylene for cooling in an ethylene plant.

Ethylene plants require refrigeration to separate out desired products from the cracking heater effluent. Typically, a $C_3$ refrigerant, usually propylene, and a $C_2$ refrigerant, typically ethylene, are used. Often, particularly in systems using low pressure demethanizers where lower temperatures are required, a separate methane refrigeration system is also employed. Thus three separate refrigeration systems are required, cascading from lowest temperature to highest. Three compressor and driver systems complete with suction drums, separate exchangers, piping, etc. are required. Also, a methane refrigeration cycle often requires reciprocating compressors which can partially offset any capital cost savings resulting from the use of low pressure demethanizers.

Mixed refrigerant systems have been well known in the industry for many decades. In these systems, multiple components are utilized in a single refrigeration system to provide refrigeration at a wider range of temperatures, enabling one mixed refrigeration system to replace multiple pure component cascade refrigeration systems. These mixed refrigeration systems have found widespread use in base load liquid natural gas plants. Articles have also been written on the application of mixed refrigeration systems to ethylene plant design but they are complicated in operation due to the multiplicity of components in the refrigerant. Also they are less efficient in the propylene refrigeration compressor cycle temperature range at –40° C. or warmer.

SUMMARY OF THE INVENTION

It is an object of the present invention, therefore, to provide a simplified refrigeration system for an ethylene plant having a low pressure demethanizer utilizing a mixture of methane and ethylene, or alternately methane and ethane, as a binary refrigerant cascading against a propylene, or alternately propane, refrigeration system. This system replaces the separate methane and ethylene refrigeration systems which are used in conjunction with a propylene refrigeration system in conventional plants and saves one compressor system. The refrigerant composition may be constant throughout the system or separators may be used to partially flash and divide the binary refrigerant into a methane rich stream and an ethylene rich stream for separate circulation in one or more heat exchangers. The objects, arrangement and advantages of the refrigeration system of the present invention will be apparent from the description which follows.

DESCRIPTION OF THE PREFERRED EMBODIMENTS

Figure 1:
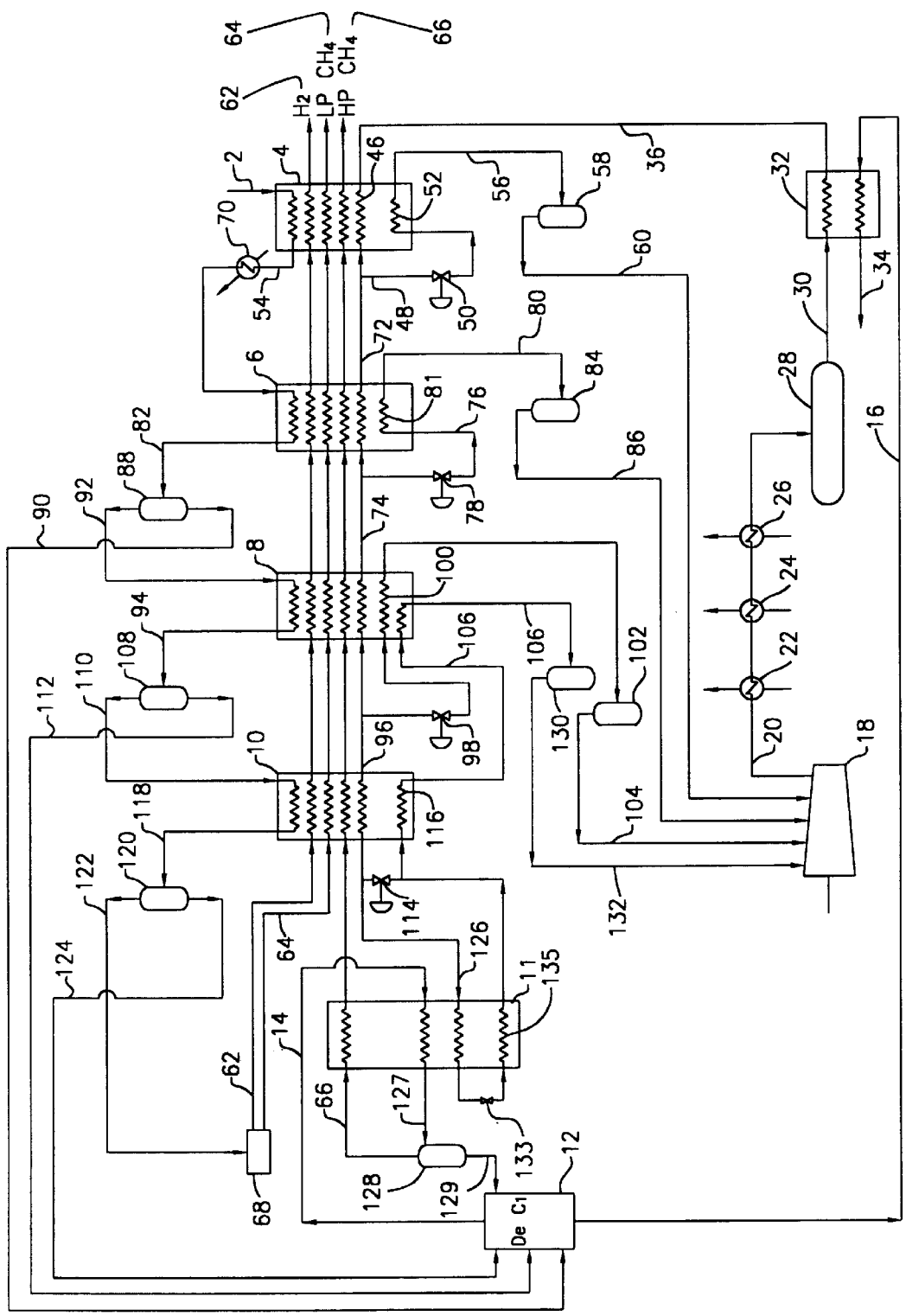
FIG. 1 is a schematic flow diagram of a portion of an ethylene plant illustrating one embodiment of the refrigeration system of the present invention.

The present invention involves an ethylene plant wherein a pyrolysis gas is first processed to remove methane and hydrogen and then processed in a known manner to produce and separate ethylene as well as propylene and some other by-products. The separation of the gases in an ethylene plant through condensation and fractionation at cryogenic temperatures requires refrigeration over a wide temperature range. The capital cost involved in the refrigeration system of an ethylene plant can be a significant part of the overall plant cost. Therefore, capital savings for the refrigeration system will significantly affect the overall plant cost.

Ethylene plants with high pressure demethanizers operate at pressures higher than 2.758 MPa (400 psi) and can produce overhead reflux by condensation against a pure component ethylene refrigeration. Demethanizer overhead temperatures of these systems are typically in the range of –85° C. to –100° C. Ethylene refrigeration at approximately –101° C. is typically used for chilling the overhead condenser. At pressures below 2.758 MPa, the overhead temperature is typically too low to use ethylene refrigeration unless a vacuum suction is used. But that is not desirable because of the capital cost increase and the safety concern due to potential air leakage into the system.

The present invention involves the use of a low pressure demethanizer and a binary refrigerant system. For purposes of the present invention, a low pressure demethanizer is one which operates below about 2.41 MPa (350 psi) and generally in the range of 0.345 to 1.034 MPa (50 to 150 psi) and with overhead temperatures in the range of –200 to –235° C. The advantage of the low pressure demethanizer is the lower total plant power requirement and lower total plant capital cost while the disadvantage is the lower refrigeration temperature required and, therefore, the need heretofore of a separate methane refrigeration compressor.

The binary refrigerant of the present invention comprises a mixture of methane and ethylene. The ratio of methane to ethylene will vary depending on ethylene plant cracking feedstock, cracking severity, chilling train pressure and the nature of the refrigerant among other considerations, but will normally be in the range of 10:90 to 50:50 and more likely in the range of 20:80 to 40:60. The use of the methane and ethylene or methane and ethane binary refrigerant, along with a propylene or propane refrigeration system, provides the refrigeration load and temperatures required for an ethylene plant having a low pressure demethanizer while obviating the need for three separate refrigerants of methane, ethylene and propylene.

A binary refrigerant would not be used with a high pressure demethanizer because there is no need to provide that level of refrigeration. There is no need to use a binary refrigeration system as a simple substitute for a pure component ethylene refrigeration system. It would just be more costly and complex. Mixed refrigerant systems to replace both the ethylene and propylene refrigeration systems have been proposed but they require at least one component lighter than the ethylene such as methane. Therefore, it is at least a ternary system. It is usually more economical to also use components heavier than propylene, such as $C_4$ components, so that the system is usually at least a quaternary refrigerant system.

The purpose of the present invention is to provide the necessary refrigeration for the charge gas (pyrolysis gas) in general to separate out the hydrogen and methane and provide a feed for the demethanizer. Referring to the embodiment of the invention shown in FIG. 1, the charge gas feed 2, which is the pyrolysis gas conditioned as required and cooled, is typically at a temperature of about –35 to –37° C. and a pressure of about 3.45 MPa (500 psi), and is typically already partially liquified.

The charge gas 2 is progressively cooled by the refrigeration system of the present invention in the heat exchangers 4, 6, 8 and 10 and separated to produce demethanizer feeds as will be explained later. The heat exchangers 4, 6, 8 and 10 are typically brazed aluminum exchangers, also called platefin or core exchangers, and can be physically combined as fewer units or expanded into a greater number of units. In the demethanizer 12, the $C_1$ and lighter components, primarily methane and hydrogen, are separated from the $C_2$ and heavier components. The net overhead 14 from the demethanizer 12 is used as a cooling stream in the refrigeration system as will be explained hereinafter. The bottoms 16 from the demethanizer can also be used as a cooling stream in another portion of the refrigeration system as will also be explained hereinafter.

Turning now to the refrigeration system per se, the binary refrigerant as identified earlier as a mixture of methane and ethylene is compressed by the refrigeration compressor 18 up to a pressure in the range of about 3.0 to 4.0 MPa. In the Table which appears later, specific pressures and temperatures for one specific example of the invention are listed. The compressed binary refrigerant 20 is cooled at 22 and 24 such as by cooling water or other cold stream and cooled still further at 26 such as by a propylene refrigerant down to a temperature in the range of about −30 to −40° C. The liquid binary coolant is collected in the receiver or accumulator 28.

The coolant 30 from the receiver 28 can be further cooled at 32 by heat exchange with the bottoms 16 from the demethanizer 12, or other cold stream being heated, which will lower the temperature. The demethanizer bottoms exiting from the heat exchanger 32 at 34 are sent to the deethanizer for the conventional production and separation of the ethylene, propylene and other by-products.

The binary refrigerant 36 from the heat exchanger 32 is then passed to the first of the series of the heat exchangers 4, 6, 8, 10 and 11. The heat exchangers 4 to 10 are the heat exchangers which provide the cooling of the charge gas from the pyrolyzer. Heat exchanger 11 provides reflux to the demethanizer.

Referring first to heat exchanger 4, the binary refrigerant 36 is passed through the heat exchange coil 46 and cooled. A portion of the binary refrigerant is then withdrawn at 48 and the temperature is dropped by lowering the pressure through the expansion valve 50. This cooled binary refrigerant portion is then passed back through the heat exchange coil 52. The expansion valve 50 is controlled in response to the temperature of the charge gas stream 54 cooled in the heat exchanger 4 thereby controlling the temperature of the refrigerant in the heat exchange coil 52. The binary refrigerant in heat exchange coil 52 absorbs heat and is vaporized and superheated up to a temperature range of 1 to 5° C. lower than incoming stream 36. The vaporized binary refrigerant 56 from the coil 52 passes to the suction drum 58 from which the refrigerant vapor stream 60 is fed to the binary refrigeration compressor 18. The suction drum 58, as well as the other suction drums 84, 102 and 130 referred to later, is present only to separate out any liquid that may be present in an upset condition to prevent potential compressor damage. It is not needed for the normal operation of the system.

The reason that the binary refrigerant is first passed through the heat exchanger 4 for cooling before flashing at 50 is to decrease the percentage of vapor flashed at a fixed flash pressure. Thus, the flashed liquid will be colder and can provide more refrigeration at colder temperatures. For a pure component refrigerant, the flashed liquid temperature is fixed for any given flashed liquid pressure and there would be no net gain from cooling before flashing. This same principal applies to the other heat exchangers 6, 8, 10 and 11.

Additional cooling in the heat exchanger 4 as well as in the other heat exchangers 6, 8 and 10 is provided by the streams 62, 64 and 66 which are low temperature streams of hydrogen, low pressure methane and high pressure methane respectively. These low temperature streams 62, 64 and 66 come from the cryogenic hydrogen/methane separation system 68 and the overhead 14 from the demethanizer 12. The net overhead stream 66 also provides chilling for heat exchanger 11 which serves as a demethanizer reflux condenser.

The cooled charge gas 54 may be further cooled at 70 and fed to the next heat exchanger 6. The cooling at exchanger 70 can be reboiling and interboiling of demethanizer 12. The remaining cooled binary refrigerant 72 from the heat exchanger 4 is also fed to the next heat exchanger 6. This heat exchanger 6 is operated in the same manner as the heat exchanger 4 except that all of the relevant temperatures are now lower including the temperatures of the incoming binary refrigerant stream 72, the exit binary refrigerant stream 74, the binary refrigerant stream 76 after the expansion valve 78, the vaporized binary refrigerant stream 80 from the coil 81 and the exit charge gas stream 82. The vaporized binary refrigerant 80 is fed to the suction drum 84 and then fed at 86 to the binary refrigeration compressor 18.

The charge gas stream 82 is fed to the separator 88 in which the cooled charge gas is separated into a less volatile demethanizer feed stream 90 and a more volatile overhead stream 92 which is now more concentrated in methane and hydrogen. The overhead 92 and the binary refrigerant 74 pass to the next heat exchanger 8 wherein the cooling process continues in the same manner producing the further cooled charge gas 94 and binary refrigerant 96. Once again, a portion of the binary refrigerant passes through the expansion valve 98 and the coil 100 to the suction drum 102. The vapor 104 is then fed to the binary refrigerant compressor 18. The heat exchanger 8 may also be further cooled by the vaporized binary refrigerant stream 106 from the heat exchanger 10.

The charge gas 94 from the heat exchanger 8 is fed to the separator 108 where the more volatile components are removed overhead at 110 and fed to the heat exchanger 10. This overhead is now even further concentrated in hydrogen and methane. The bottoms from the separator 108 are fed at 112 to the demethanizer 12.

The cooling process continues in the heat exchanger 10 by the expansion of an additional portion of the binary refrigerant through the expansion valve 114 and the vaporization in coil 116 to produce the binary refrigerant stream 106 previously mentioned. The exit charge gas 118 is fed to the separator 120 with the overhead 122 now being primarily hydrogen and methane. The overhead 122 is fed to the hydrogen/methane separation system 68 where the hydrogen and methane are cryogenically separated to produce the hydrogen stream 62 and the low pressure methane stream 64. The bottoms from the separator 120 are fed at 124 to the demethanizer 12. The now remaining binary refrigerant stream 126 is further cooled in the heat exchanger 11 by the demethanizer net overhead 66. The binary refrigerant stream 126 is expanded at 133 and passed back through the coil 135 in heat exchanger 11 to be mixed with the refrigerant from valve 114.

The gross overhead stream 14 from the demethanizer 12 goes to the heat exchanger 11 where it is partially condensed. This partially condensed stream 127 flows to the separator 128. Liquid 129 from the separator 128 flows back to the demethanizer 12 as reflux. The overhead 66 from separator 128 is now the net demethanizer overhead comprising primarily methane which is reheated by passing back through the heat exchangers 11, 10, 8, 6 and 4. The demethanizer column 12 has the typical reboiler and interreboilers between stages which have not been shown. The bottoms 16 of the demethanizer is C$_2$ and heavier components. Reboiling and interreboiling are typically provided by cooling of the charge gas such as by the heat exchanger 70.

Stream 106 goes to suction drum 130 and then at 132 to the binary refrigerant compressor 18. Although FIG. 1 illustrates four heat exchangers 4, 6, 8 and 10, the number of these heat exchangers can vary depending on the particular needs for any particular ethylene process and in particular on the particular charge gas. The following Table lists temperatures and some pressures for the binary refrigerant and for the charge gas (process gas) including the demethanizer system at various locations in the process flow scheme of FIG. 1 for one specific example:

|  | Location | T - °C. | Pressure - MPa |
| --- | --- | --- | --- |
| Binary Refrigerant | 28 | −37 | 4.5 |
|  | 58 | −48 | 1.6 |
|  | 84 | −65 | 0.8 |
|  | 102 | −75 | 0.5 |
|  | 130 | −106 | 0.02 |
| Process Gas | 66 | −133 | 0.6 |
|  | 2 | −37 | 3.5 |
|  | 62 | −135 | — |
|  | 92 | −72 | — |
|  | 110 | −91 | — |
|  | 122 | −132 | — |

Some of the advantages of the binary refrigerant system of the present invention have been previously mentioned and include a reduction in the number of compressor systems and the ability to use all centrifugal or axial compressors instead of a methane reciprocating compressor. A further advantage is that the binary refrigerant composition is easier to maintain than a more complicated mixed refrigerant containing three or more components. This is most evident in the event of a system trip or upset which results in the venting of refrigerant. The venting process results in the loss of more of the lighter components of the refrigerant than of the heavier components. This changes the ratio of the components which must be corrected upon restart. The more complicated the refrigerant composition, the more difficult it is to correct the ratio.

In the process of the present invention depicted in FIG. 1 the composition of the refrigerant remains constant throughout the process. However, in the alternate embodiment of the invention depicted in FIG. 2, there is a separation of the binary refrigerant into a binary methane-rich stream and a binary ethylene-rich stream.

Figure 2:
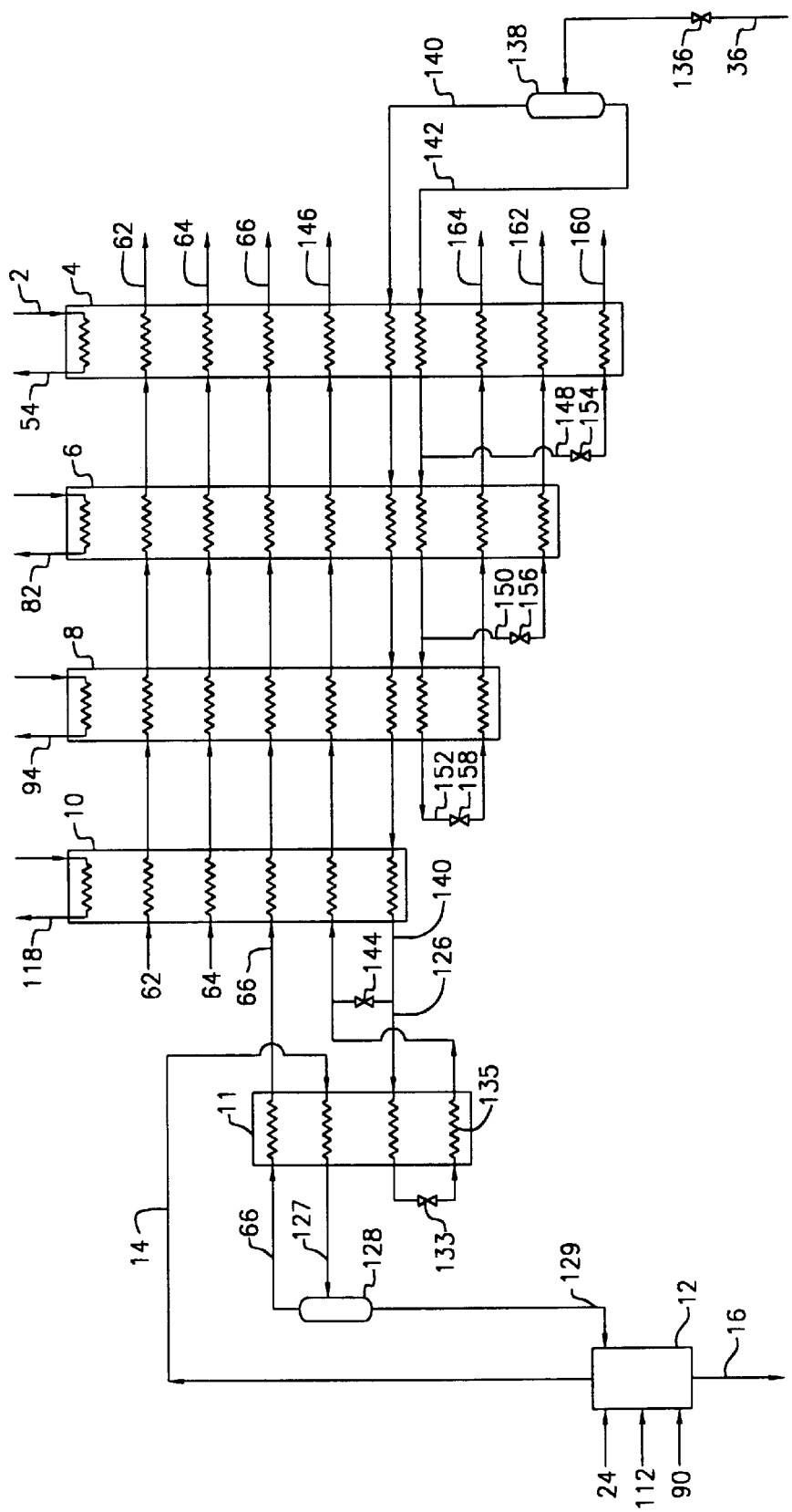
FIG. 2 is a schematic flow diagram similar to FIG. 1 but illustrating an alternate embodiment of the invention.

In FIG. 2, which generally shows only the portion of FIG. 1 which is modified, an expansion valve 136 is located in the line 36. The pressure of the binary refrigerant drops and a portion is vaporized. The liquified portion and the vapor portion are separated in the flash tank 138 whereby the vapor portion 140 will be rich in methane and the liquid portion 142 will be rich in ethylene or ethane. In this FIG. 2 embodiment, the methane-rich stream 140 passes through all of the heat exchangers 4, 6, 8 and 10 and a portion is then expanded at 144 and passed back as stream 146 through all of the heat exchangers 10, 8, 6 and 4. Another portion 126 of stream 140 leaving exchanger 10, is cooled in exchanger 11, expanded at 133 and passed back through exchanger 11 and joins stream 146 at the inlet of exchanger 10. The exit methane-rich binary refrigerant stream 146 would then be passed back to the first stage of the compressor 18. The ethylene-rich stream 142 is handled somewhat like the binary refrigerant stream in FIG. 2 in that a portion is withdrawn after each of the first three heat exchangers at 148, 150 and 152 and expanded at 154, 156 and 158. The expanded portions are then passed back through one or more of the heat exchangers to produce the exit ethylene- or ethane-rich binary refrigerant stream 160, 162 and 164 which are fed back to the appropriate compressor stages.

The advantage of the FIG. 2 scheme where the binary refrigerant is separated is that it enables a higher pressure at the compressor suction for any given binary refrigerant composition at the compressor outlet. The suction pressure is higher because the refrigerant composition is richer in methane and, therefore, for a fixed refrigerant temperature, the pressure will be higher. This means that the compression ratio of the compressor is lower and this can result in a decreased compressor cost.

A variation of FIG. 2 has no valve 136 in line 36. Rather, the pressure in line 36 is lowered such that the stream is not completely liquified and a vapor portion remains. Separator 138 separates the condensed liquid portion from the methane-enriched vapor portion. This variation allows compressor 18 to have a lower discharge pressure for any given methane-ethylene (or methane-ethane) composition for stream 36. The overall compression ratio for compressor 18 is lowered. The flow rate of stream 36 increases to compensate for any given stream 36 composition. Compressor costs can however decrease. This scheme is particularly of interest for smaller ethylene plants where the actual compressor volume at the discharge of compressor 18 approaches the lower limit allowable by centrifugal compressor design.

Figure 3:
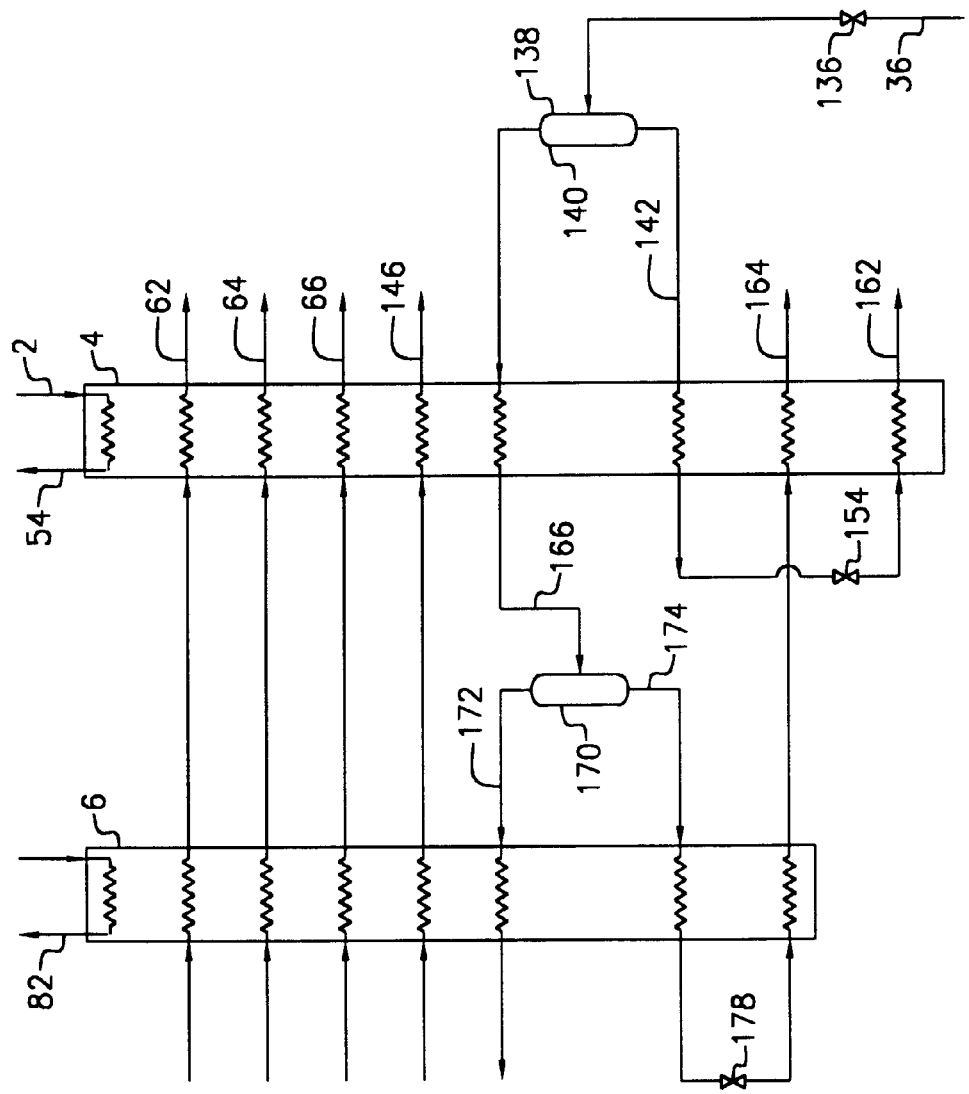
FIG. 3 is a schematic flow diagram illustrating a variation of the FIG. 2 embodiment.

FIG. 3 is a still further modification of the present invention similar to the embodiment shown in FIG. 2 but with an additional separation step for the binary refrigerant. As shown, there is the first separation at 138 just as in the FIG. 2 embodiment. The methane-rich binary refrigerant vapor stream 140 is passed through the heat exchanger 4, partially liquified, and then passes through the line 166 to the additional refrigerant separator 170 where the refrigerant is again separated into a second methane-rich vapor stream 172 and a second ethylene- or ethane-rich liquid stream 174. The methane-rich stream 172 will be richer in methane than stream 174 and stream 140. The ethylene- or ethane-rich stream 142 passes through the heat exchangers just as in the FIG. 2 embodiment. Likewise, the second methane-rich stream 172 is passed through the second heat exchanger 6, and then flows to lower temperature heat exchangers as in the other embodiments where it is expanded and passed back through the heat exchangers. The second ethylene- or ethane-rich stream 174 is passed through the second heat exchanger, expanded at 178 and passed back through the heat exchanger. This FIG. 3 illustrates only two heat exchangers for simplicity but there could be additional heat exchangers and additional separators similar to separator 170.

The advantage of this FIG. 3 process variation is that binary refrigerant pressures are higher at any given refrigeration temperature level. This decreases compression ratios in the binary refrigerant compressor and can reduce compressor capital cost.

We claim:

1. In a process for the production of ethylene from a charge gas containing hydrogen, methane, ethylene and other $C_2$ and heavier hydrocarbons wherein said process includes a low pressure demethanizer operating at a pressure below 2.41 MPa (350 psi) and wherein said charge gas is cooled by a refrigeration system, a method for cooling said charge gas by the use of a binary refrigerant in said refrigeration system comprising the steps of compressing a mixture of methane and ethylene or methane and ethane to produce a binary refrigerant, progressively expanding and cooling said binary refrigerant through a series of heat exchangers, progressively bringing said progressively cooled binary refrigerant and said charge gas into heat exchange contact in said heat exchangers to cool and thereby separate said hydrogen and a portion of said methane and produce liquid demethanizer feed streams concentrated in said ethylene and other $C_2$ and heavier hydrocarbons, feeding said liquid demethanizer feed streams to said low pressure demethanizer and producing a gross demethanizer overhead stream consisting essentially of methane, contacting said gross demethanizer overhead stream with said progressively cooled binary refrigerant and separating out a demethanizer reflux stream and a net demethanizer overhead stream and returning said demethanizer reflux stream to said demethanizer.

2. In a process as recited in claim 1 wherein said net demethanizer overhead stream is brought into heat exchange contact with said charge gas in said heat exchangers.

3. In a process as recited in claim 1 wherein said hydrogen and said portion of said methane separated from said charge gas by cooling in said heat exchangers are subjected to cryogenic separation to produce a hydrogen stream and a methane stream and wherein said hydrogen and methane streams are each brought into heat exchange contact with said charge gas in said heat exchangers.

4. In a process as recited in claim 1 wherein step of progressively expanding and cooling said binary refrigerant through a series of heat exchangers comprises the steps of passing said binary refrigerant through one of said heat exchangers, expanding a portion of said binary refrigerant after passage through said one heat exchanger, passing said expanded portion back through said one heat exchanger and passing the remaining portion of said binary refrigerant to and through the next one of said heat exchangers and repeating said step of expanding a further portion and passing said further portion back through said heat exchanger.

5. In a process as recited in claim 4 wherein said portions of said binary refrigerant after passing back through said heat exchangers are passed back to the step of compressing said binary refrigerant.

6. In a process as recited in claim 1 wherein said demethanizer feed streams separated by each of said heat exchangers are each fed to different stages of said demethanizer.

7. In a process as recited in claim 1 and further including the step of separating said binary refrigerant into a methane-rich binary refrigerant and an ethylene- or ethane-rich binary refrigerant and wherein said step of progressively contacting said progressively cooled binary refrigerant with said change gas comprises the step of contacting said change gas with separate streams of said methane-rich binary refrigerant and said ethylene- or ethane-rich binary refrigerant in said heat exchangers.

8. In a process as recited in claim 7 and further including the step of separating said methane-rich binary refrigerant into a second methane-rich binary refrigerant and a second ethylene- or ethane- rich binary refrigerant and wherein said step of contacting said charge gas comprises the step of also contacting said charge gas with separate streams of said second methane-rich binary refrigerant and said second ethylene- or ethane-rich binary refrigerant.

9. In a process as recited in claim 7 wherein said step of compressing said mixture of methane and ethylene or methane and ethane comprises the step of compressing to form a liquid-vapor mixture and wherein said liquid-vapor mixture is separated to form said methane-rich binary refrigerant and said ethylene- or ethane-rich binary refrigerant.

\* \* \* \* \*